(12) United States Patent
McMinn et al.

(10) Patent No.: US 7,439,204 B2
(45) Date of Patent: Oct. 21, 2008

(54) PROCESS FOR PRODUCING CATALYSTS WITH REDUCED HYDROGENATION ACTIVITY AND USE THEREOF

(75) Inventors: Timothy E. McMinn, Houston, TX (US); Ronald J. Cimini, Friendswood, TX (US); Robert A. Crane, Lumberton, TX (US); Andrew M. Hiester, Houston, TX (US); Teresa A. Jurgens-Kowal, Seabrook, TX (US); Gary D. Mohr, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 318 days.

(21) Appl. No.: 10/800,888

(22) Filed: Mar. 15, 2004

(65) Prior Publication Data

US 2005/0202955 A1   Sep. 15, 2005

(51) Int. Cl.
   *B01J 29/06*   (2006.01)
(52) U.S. Cl. .......................................... 502/74; 502/77
(58) Field of Classification Search .................. 502/74, 502/77, 85
   See application file for complete search history.

(56) References Cited

U.S. PATENT DOCUMENTS

| | | | |
|---|---|---|---|
| 3,201,356 A | 8/1965 | Kress et al. | |
| 4,163,028 A | 7/1979 | Tabak et al. | |
| 4,331,822 A | 5/1982 | Onodera et al. | |
| 4,415,441 A | 11/1983 | Markley et al. | |
| 4,695,666 A | 9/1987 | Chao et al. | |
| 5,004,855 A | 4/1991 | Tada et al. | |
| 5,672,796 A * | 9/1997 | Froment et al. | 585/419 |
| 5,990,365 A * | 11/1999 | Chang et al. | 585/475 |
| 6,576,582 B1 * | 6/2003 | Beck et al. | 502/71 |
| 2002/0091293 A1 * | 7/2002 | Chang et al. | 585/906 |
| 2003/0036670 A1 | 2/2003 | Seung-Hoon et al. | |

FOREIGN PATENT DOCUMENTS

| | | |
|---|---|---|
| DE | 221752 | 5/1985 |
| EP | 0 307 113 | 3/1989 |
| EP | 0 923 989 | 6/1999 |
| GB | 1332349 | 10/1973 |

OTHER PUBLICATIONS

Parera, J.M., et al., "Hydrogenolysis Passivation of Reforming Catalysts by Hydrogen Pretreatment", Applied Catalysis, 12 (1984) pp. 125-139, Elsevier Science Publishers B.V., Amsterdam—Printed in the Netherlands, no month.

Kubicka, H., et al., "The influence of thermal pretreatment of Re/y-alumina catalysts in hydrogen on their activity for hydrogenation and hydrogenolysis of benzene", Catalysis Letters 25 (1994), pp. 157-162, J.C. Baltzer AG, Science Publishers, no month.

Okal, J., et al., "Influence of oxidation-reduction treatment on activity and selectivity of Re supported on y-alumina", Applied Catalysis A: General 171 (1998), pp. 351-359, Elsevier Science B.V., no month.

Kubicka, H., et al., "The Dispersity of y-Alumina Supported Rhenium from Hydrogen Pulse Chemisorption", React. Kinet. Catal. Letters, vol. 48, No. 1, pp. 195-200 (1992), Akademaiai Kiado, Budapest, no month.

Oyekan, S.O. et al., "Optimized Pretreatment Procedures for Reforming Catalysts", prepared for presentation at 1991 Spring National Meeting of the AIChE, Houston, Apr. 11, 1991.

Yates, D.J.C. et al., "An Investigation of the Dispersion and Catalytic Properties of Supported Rhenium", Journal of Catalysis 14, pp. 182-186 (1969), Corp. Res. Lab., Esso Res. and Eng. Co., Linden, NJ USA, no month.

Yamada, M. et al., "Hydrogenolysis of Methylcyclpentane by Supported PT/RE Catalysts", Journal JPN Pet. Inst. vol. 25, No. 2, pp. 112-117 (Mar. 1982) Tohoku University, Japan.

Okal, J. et al., "Influence of oxidation-reduction treatment on activity of Re/y-Al2O3 catalyst diluted with y-alumina", Applied Catalysis A: General 209 (2001) pp. 375-381, Elsevier Science B.V., no month.

Kubicka H. et al., "Specific activity of y-alumina supported rhenium for hydrogenation and hydrogenolysis of benzene in relation to metal concentration and dispersity", React. Kinet. Catal. Lett, 34, No. 2, pp. 433-438 (1987), Aka Kiado, Budapest, no month.

"Metal catalysts.35. Catalytic properties of platinum-rhenium/aluminum oxide and platinum-iridium/aluminum oxide catalysts in hydrocarbon conversions," Siegfried et al., Chemische Technik (Leipzig, Germany) (1984), 36(3), 101-104, no month.

* cited by examiner

*Primary Examiner*—Elizabeth D Wood
(74) *Attorney, Agent, or Firm*—Andrew B. Griffis

(57) ABSTRACT

A process for controlling the hydrogenation activity of a catalyst comprised of a crystalline molecular sieve and at least one hydrogenation metal selected from the group consisting of a Group VIIB metal, a Group VIII metal, and mixtures thereof. The process is carried out by contacting the catalyst with hydrogen under sufficient conditions of temperature and pressure and for sufficient time to reduce the hydrogenolysis activity of the catalyst. The catalyst prepared by the process finds application in the catalytic conversion of organic compounds, such as ethylbenzene dealkylation, xylenes isomerization, and the transalkylation of polyalkylaromatic hydrocarbons.

27 Claims, No Drawings

US 7,439,204 B2

PROCESS FOR PRODUCING CATALYSTS WITH REDUCED HYDROGENATION ACTIVITY AND USE THEREOF

FIELD OF THE INVENTION

This invention relates to a process for producing catalysts with reduced hydrogenation activity and the use of the catalysts prepared by the process as catalysts in the catalytic conversion of organic compounds.

BACKGROUND OF THE INVENTION

Hydrogenation involves adding one or more hydrogen atoms to an unsaturated hydrocarbon (e.g., an olefin or aromatic compound). Hydrogenation can occur either as direct addition of hydrogen to the double bonds of unsaturated molecules, resulting in a saturated product, or it may cause the breaking of the bonds of organic compounds, with subsequent reaction of hydrogen with the molecular fragments. Examples of the first type (called addition hydrogenation) are the conversion of aromatics to cycloparaffins and the hydrogenation of unsaturated olefins, e.g., ethylene, to saturated olefins, e.g., ethane, by addition of hydrogen to the double bonds. Examples of the second type (called hydrogenolysis or hydrocracking) are the cracking of petroleum and hydrogenolysis of light hydrocarbon gases, e.g., ethane, to methane.

Some addition hydrogenation reactions, such as conversion of aromatics to cycloparaffins, are structure sensitive reactions. Structure sensitive reactions have reaction rates that are dependent upon the size of the active catalyst sites. Hydrogenolysis reactions can also be structure sensitive.

Hydrogenation is typically carried out in the presence of a catalyst comprised of a support, such as a natural clay, a synthetic metal oxide, or a crystalline molecular sieve such as zeolite, and a metal hydrogenation component.

Catalysts having a hydrogenation function are employed in a wide variety of organic compound conversion processes. An example of such a process involves the isomerization of xylene and dealkylation of ethylbenzene to benzene and ethane. This process is typically carried out by passing a para-xylene depleted $C_8$ aromatic feed containing ethylbenzene over a catalyst comprised of a molecular sieve support, e.g., intermediate pore size molecular sieve, and a hydrogenation component, such as a Group VIII metal, e.g., platinum, or a Group VIIB metal, e.g., rhenium, to obtain ortho-, meta-, and para-xylene in a ratio approaching the equilibrium value while converting the ethylbenzene to benzene and ethane. The hydrogenation component is present in the catalyst to hydrogenate the ethylene formed in the dealkylation of ethylbenzene to ethane. An example of such a process is disclosed in U.S. Pat. No. 4,163,028.

It is important that the catalysts used in many organic compound conversion processes, such as xylenes isomerization/ethylbenzene conversion processes, have reduced hydrogenation activity. For example, if the catalyst used in xylenes isomerization/ethylbenzene dealkylation has hydrogenolysis activity that is too high, ethylene formed in the dealkylation of ethylbenzene to ethylene and benzene can be cracked to methane. This cracking reaction generates a large amount of heat, which can cause large exotherms inside the reactor, which can lead to damage of the catalyst, equipment, or both.

Also, in reactions involving aromatics conversion, catalysts having too high addition hydrogenation activity can result in aromatic ring saturation. Aromatic ring saturation results in aromatic molecules being converted to naphthene. These naphthenes can crack to light hydrocarbon gases when contacted with acid-based catalysts. Ring saturation can result in the loss of high value aromatics, e.g., xylenes.

One technique for passivating the catalyst (lowering the hydrogenation activity of the catalyst) involves treating the catalyst with a sulfur-containing compounds such as hydrogen sulfide gas or an organic sulfide compound. Such a technique is disclosed in U.S. Pat. No. 5,004,855.

When a sulfur treatment technique is used to reduce the hydrogenation activity of a catalyst, certain problems can arise. For instance, treatments using sulfur involve a toxic, corrosive, and pungent substance. Also, when the support material used in the catalyst is a molecular sieve having unidimensional ring pores, the sulfur treatment can block the pores of the molecular sieve, which usually results in reduced activity (and even deactivation) of the catalyst.

The present invention provides a process for reducing the hydrogenation activity of a catalyst that avoids treating the catalyst with sulfur compounds.

SUMMARY OF THE INVENTION

In accordance with the present invention, there is provided a process for reducing the hydrogenation activity of a catalyst comprising a crystalline molecular sieve and at least one hydrogenation metal selected from the group consisting of a Group VIIB metal, a Group VIII metal, and mixtures thereof. The process is carried out by contacting the catalyst with hydrogen under sufficient conditions of temperature and pressure and for sufficient time to reduce the hydrogenation activity of the catalyst.

In another embodiment, the present invention provides a process for the converting of organic compounds, e.g., hydrocarbons, by contacting the organic compounds under conversion conditions with the hydrogen treated catalyst. Examples of such conversion processes include ethylbenzene dealkylation, xylenes isomerization/ethylbenzene dealkylation, and aromatics transalkylation.

DETAILED DESCRIPTION OF THE INVENTION

Support

Examples of supports suitable for use in the present invention include naturally occurring and synthetic crystalline molecular sieves. Examples of such molecular sieves include large pore molecular sieves, intermediate size pore molecular sieves, and small pore molecular sieves. These molecular sieves are described in "Atlas of Zeolite Framework Types", eds. Ch. Baerlocher, W. H. Meier, and D. H. Olson, Elsevier, Fifth Edition, 2001, which is hereby incorporated by reference. A large pore molecular sieves generally has a pore size of at least about 7 Å and includes IWW, LTL, VFI, MAZ, MEI, FAU, EMT, OFF, *BEA, and MOR structure type molecular sieves (IUPAC Commission of Zeolite Nomenclature). Examples of large pore molecular sieves, include ITQ-22, mazzite, offretite, zeolite L, VPI-5, zeolite Y, zeolite X, omega, Beta, ZSM-3, ZSM-4, ZSM-18, ZSM-20, SAPO-37, and MCM-22. An intermediate pore size molecular sieve generally has a pore size from about 5 Å to about 7 Å and includes, for example, ITH, ITW, MFI, MEL, MTW, EUO, MTT, HEU, FER, MFS, and TON structure type molecular sieves (IUPAC Commission of Zeolite Nomenclature). Examples of intermediate pore size molecular sieves, include ITQ-12, ITQ-13, ZSM-5, ZSM-12, ZSM-22, ZSM-23, ZSM-34, ZSM-35, ZSM-38, ZSM-48, ZSM-50, ZSM-57, silicalite, and silicalite 2. A small pore size molecular sieve has a pore size from about 3 Å to about 5 Å and includes, for example, CHA, ERI, KFI, LEV, and LTA structure type molecular sieves (IUPAC Commission of Zeolite Nomenclature). Examples of small pore molecular sieves include ZK-4, SAPO-34, SAPO-35, ZK-14, SAPO-42, ZK-21, ZK-22, ZK-5, ZK-20, zeolite A, erionite, chabazite, zeolite T, gmelinite, and clinoptilolite.

The framework atoms of the molecular sieves will include at least one element, usually two elements, selected from the group consisting of Si, Al, P, Ge, Ga and Ti.

When the molecular sieve is a zeolitic-type molecular sieve, the molecular sieve will comprise compositions that have the following molar relationship:

$$X_2O_3:(n)YO_2,$$

wherein X is a trivalent element, such as boron, aluminum, iron, and/or gallium, Y is a tetravalent element such as silicon, tin, and/or germanium, and n has a value of at least 2, said value being dependent upon the particular type of molecular sieve and the trivalent element present in the molecular sieve.

When the molecular sieve is a zeolitic-type intermediate pore size molecular sieve, the molecular sieve preferably comprises a composition having the following molar relationship:

$$X_2O_3:(n)YO_2,$$

wherein X is a trivalent element, such as aluminum, and/or gallium, Y is a tetravalent element such as silicon, tin, and/or germanium; and n has a value greater than 10, said value being dependent upon the particular type of molecular sieve and the trivalent element present in the molecular sieve. When the molecular sieve has a MFI structure, n is preferably greater than 20. When X is aluminum and Y is silicon, the molecular sieve is an aluminosilicate zeolite. When X is gallium and Y is silicon, the molecular sieve is a gallosilicate molecular sieve.

When the molecular sieve is a gallosilicate intermediate pore size molecular sieve, the molecular sieve preferably comprises a composition having the following molar relationship:

$$Ga_2O_3:ySiO_2$$

wherein y is between about 24 and about 500. The molecular sieve framework may contain only gallium and silicon atoms or may also contain a combination of gallium, aluminum, and silicon.

Hydrogenation Metal

The molecular sieve support will contain at least one hydrogenation metal selected from the group consisting of a Group VIII metal (i.e., Pt. Pd, Ir, Rh, Os, Ru, Ni, Co and Fe), a Group VIIIB metal (i.e., Mn, Tc and Re), and mixtures thereof. Reference to the hydrogenation metal or metals is intended to encompass such metal or metals in the elemental state (i.e. zero valent) or in some other catalytically active form such as an oxide, sulfide, halide, carboxylate and the like. The preferred hydrogenation metal is rhenium.

The hydrogenation component may be incorporated or intimately associated with the molecular sieve support by techniques known in the art such as ion-exchange, impregnation or physical admixture. For example, solutions of appropriate metal salts may be contacted with the catalyst components. The metal containing salt is conveniently water-soluble. Examples of suitable salts include chloroplatinic acid, tetraamineplatinum complexes, platinum chloride, rhenium oxide, and rhenium pentachloride. After incorporation of the metal, the catalyst can then be filtered, washed with water and calcined at temperatures of from about 250 to about 500° C.

The amount of hydrogenation component may be that amount which imparts or increases the catalytic ability of the overall catalyst to catalytically hydrogenate or dehydrogenate an organic compound under sufficient hydrogenation or dehydrogenation conditions, e.g., hydrogenate ethylene to ethane. This amount is referred to as a catalytic amount. Usually, the amount of hydrogenation metal present will be from about 0.001 to about 10 percent by weight, e.g, from about 0.03 to about 3 percent by weight, such as from about 0.2 to about 1 percent by weight of the total catalyst although this will, of course, vary with the nature of the metal, with less of the highly active noble metals, particularly platinum, being required than of the less active base metals.

Binder

In addition, it may be desirable to combine the molecular sieve with another material resistant to the temperature and other conditions of the process. Such matrix materials include synthetic or naturally occurring substances as well as inorganic materials such as clay, silica, and/or metal oxides. The metal oxides may be naturally occurring or in the form of gelatinous precipitates or gels including mixtures of silica and metal oxides. Naturally occurring clays which can be composited with the molecular sieve include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the molecular sieves employed herein may be composited with a porous matrix material, such as alumina, silica-alumina, silica-magnesia, silica-zirconia, silica-thoria, silica-berylia, silica-titania, as well as ternary compounds such as silica-alumina-thoria, silica-alumina-zirconia, silica-alumina-magnesia, and silica-magnesia-zirconia. A mixture of these components could also be used. The matrix may be in the form of a cogel. Further, the molecular sieve may also be composited with molecular sieve material, such as the molecular sieve material disclosed in U.S. Pat. No. 6,008,425, which is hereby incorporated by reference.

The relative proportions or amount of molecular sieve and matrix material on an anhydrous basis may vary widely with the molecular sieve content usually ranging from between about 1 to about 99 percent by weight and more usually in the range of about 10 to about 80 percent by weight based on the weight of the catalyst.

Selectivation

To make the molecular sieve selective to the production of para-xylene (versus the other xylene isomers) and/or to reduce reactions on the surface of the molecular sieve, the molecular sieve catalyst, e.g., ZSM-5 catalyst, can be selectivated by the use of a selectivating agent. The term "selectivating agent" is used herein to indicate substances which will increase the shape-selectivity (i.e., para-selectivity) of the catalyst.

Examples of compounds for selectivating the catalysts include treating the surface of the catalyst with compounds of phosphorus and/or various metal oxides such as alkaline earth metal oxides, e.g., calcium oxide, magnesium oxide, etc. rare earth metal oxides, lanthanum oxide, and other metal oxides such as boron oxide, titania, antimony oxide, silica, and manganese oxide. Selectivation can also be accomplished by depositing coke on the catalyst.

Selectivation of the catalyst may also be accomplished using organosilicone compounds. The silicon compounds may comprise a polysiloxane include silicones, a siloxane, and a silane including disilanes and alkoxysilanes.

Silicone compounds that can be used in the present invention include the following:

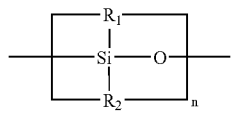

wherein $R_1$ is hydrogen, fluoride, hydroxy, alkyl, aralkyl, alkaryl or fluoro-alkyl. The hydrocarbon substituents generally contain from 1 to about 10 carbon atoms and preferably are methyl or ethyl groups. $R_2$ is selected from the same group as $R_1$, and n is an integer of at least 2 and generally in the range of 2 to about 1000. The molecular weight of the silicone compound employed is generally between about 80 to about 20,000 and preferably about 150 to about 10,000. Representative silicone compounds include dimethylsilicone, diethylsilicone, phenylmethylsilicone, methyl hydrogensilicone, ethylhydrogensilicone, phenylhydrogensilicone, fluoropropylsilicone, ethyltrifluoroprophysilicone, tetrachlorophenyl methyl methylethylsilicone, phenylethylsilicone, diphenylsilicone, methyltrisilicone, tetrachlorophenylethyl silicone, methylvinylsilicone and ethylvinylsilicone. The silicone compound need not be linear but may be cyclic as for example hexamethylcyclotrisiloxane, octamethylcyclotetrasiloxane, hexaphenyl cyclotrisiloxane and octaphenylcyclotetrasiloxane. Mixtures of these compounds may also be used as well as silicones with other functional groups.

Useful siloxanes and polysiloxanes include as non-limiting example hexamethylcyclotrisiloxane, octamethylcyclotetrasiloxane, decamethyl cyclopentasiloxane, hexamethyldisiloxane, octamethytrisiloxane, decamethyltetrasiloxane, hexaethylcyclotrisiloxane, octaethylcyclo tetrasiloxane, hexaphenylcyclotrisiloxane and octaphenylcyclo-tetrasiloxane.

Useful silanes, disilanes, or alkoxysilanes include organic substituted silanes having the general formula:

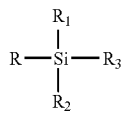

wherein R is a reactive group such as hydrogen, alkoxy, halogen, carboxy, amino, acetamide, trialkylsilyloxy, $R_1$, $R_2$ and $R_3$ can be the same as R or can be an organic radical which may include alkyl of from 1 to about 40 carbon atoms, alkyl or aryl carboxylic acid wherein the organic portion of alkyl contains 1 to about 30 carbon atoms and the aryl group contains about 6 to about 24 carbons which may be further substituted, alkylaryl and arylalkyl groups containing about 7 to about 30 carbon atoms. Preferably, the alkyl group for an alkyl silane is between about 1 and about 4 carbon atoms in chain length. Mixtures may also be used.

The silanes or disilanes include, as non-limiting examples, dimethylphenylsilane, phenylrimethylsilane, triethylsilane and hexamethyldislane. Useful alkoxysilanes are those with at least one silicon-hydrogen bond.

Selectivation of the catalyst can also be accomplished using a combination of coke, metal oxides, phosphorus compounds, and silicon applied by the procedures described above.

Hydrogen Treatment

As used herein, the expression "reduction of hydrogenation activity" means that the hydrogenation activity of the catalyst, i.e., the hydrogenation activity, the hydrogenolysis activity, or both, is lower than the hydrogenation activity of catalyst without treatment of hydrogen.

To reduce the hydrogenation activity, the catalyst is treated with hydrogen. The temperature, pressure, and time of the treatment will depend on a number of factors including the catalyst treated and the process the catalyst is to be used. The hydrogen treatment can take place before the catalyst is put on stream for organic compound conversion or after the catalyst has been put on stream.

It has been found that hydrogenation activity reduction is promoted by a positive hydrogen pressure and temperatures above ambient temperature. The pressure used in the treatment will usually be at least 700 kPa (100 psia), preferably at least 1034 kPa (150 psia), and, more preferably, at least 1400 kPa (200 psia). The temperatures used in the treatment will usually be at least 316° C. (600° F.), preferably at least 371° C. (700° F.), more preferably at least 427° C. (800° F.), and, even more preferably, at least 482° C. (900° F.). The time of the treatment will be a time sufficient to allow hydrogen to form chemical bonds with the hydrogenation metal. Usually, the treatment time will be over one hour, such as at least four hours, preferably, at least 8 hours, more preferably at least 12 hours, and most preferably at least 16 hours.

The hydrogen treatment will usually result in the catalyst having at least 10 percent less addition hydrogenation activity in comparison to the untreated catalyst. Preferably, the hydrogen treatment will result in the catalyst having at least 40 percent less addition hydrogenation activity, and, more preferably, at least 70 percent less addition hydrogenation activity, and most preferably at least 90 percent less addition hydrogenation activity. In determining the amount of addition hydrogenation activity reduction, the catalyst is preferably tested before hydrogen treatment and after hydrogen treatment using the same set of conditions.

Procedures for determining the addition hydrogenation activity are known to persons skilled in the art. For example, addition hydrogenation activity can be determined by quantifying the molar amount of aromatic rings saturated. Another more qualitative indicator of aromatic ring saturation activity is by determining product benzene purity. The purity of the benzene product in xylene isomerization applications is reduced by aromatic ring saturation reactions such as benzene being converted to cyclohexane or methylcyclopentane. Higher product benzene purity means that less aromatic ring saturation is taking place. One further indicator of aromatic ring saturation is the line-out time or "de-edging" time. The line-out time is the time it takes for the ring saturation activity of a catalyst to subside. When the hydrogen treatment procedure is applied to a hydrogenation metal containing catalyst, the "de-edging" time can be reduced. The shorter the "de-edging" time the less time the catalyst is converting valuable aromatic rings to less valuable products such as naphthenes and light hydrocarbon gases.

A preferred technique for determining the addition hydrogenation activity of the catalyst is measuring the benzene hydrogenation activity (BHA) of the catalyst. The BHA is the zero order rate constant for the hydrogenation activity of the catalyst for benzene at atmospheric pressure and 100° C. The BHA value is defined as the number of moles of benzene converted per mole of hydrogenation metal on the catalyst per second. The BHA values are preferably determined at atmospheric pressure over a fixed bed of a catalyst sample at a hydrogen to benzene molar ratio of 200:1 and a WHSV based on benzene of 500 hr$^{-1}$. Prior to contacting the catalyst sample with the benzene/hydrogen mixture, the sample is purged with helium at room temperature. Next, the benzene/hydrogen mixture is introduced and then the temperature is progressively raised from 50° C. to 75° C., then to 100° C. and finally to 125° C. Conversion measurements are made at each temperature and an Arrhenius plot is generated and used to determine the rate constant at 100° C.

The hydrogen treatment will usually result in the catalyst having at least 25 percent less hydrogenolysis activity in comparison to the untreated catalyst. Preferably, the hydrogen treatment will result in the catalyst having at least 50 percent less hydrogenolysis activity, and, more preferably, at least 75 percent less hydrogenolysis activity. Most preferably, the catalyst after treatment is substantially free of hydrogenolysis activity. In determining the amount of hydrogenolysis activity reduction, the catalyst is preferably tested before hydrogen treatment and after hydrogen treatment using the same set of conditions.

Procedures for determining the hydrogenolysis activity are known to persons skilled in the art. For example, the hydrogenolysis activity of the catalyst can be determined by measuring the ethane cracking activity (ECA) of the catalyst. The ECA value is determined by measuring the amount of ethane converted to methane. Preferably, the ECA test is run at atmospheric pressure over a fixed bed of a catalyst at a hydrogen to ethane molar ratio of 200:1 and a WHSV based on ethane of 2000 hr$^{-1}$. Prior to contacting the catalyst sample with the ethane/hydrogen mixture, the sample is purged with helium at room temperature. Next, the ethane/hydrogen mixture is introduced and then the temperature is progressively raised from 50° C. to 100° C. to, then to 200° C. and finally to 500° C. Conversion measurements are made at each temperature and an Arrhenius plot is generated and used to determine the rate constant at 500° C.

Although not bound by any theory of operation, it is believed that hydrogenation hydrogenolysis activity reduction occurs because of hydrogen chemically bonding to the hydrogenation metal atoms. The amount of these bonds that form is dependent upon the hydrogenation metal present in the catalyst, the hydrogen pressure, the temperature and the duration of the hydrogen exposure to the hydrogenation metal. In line with this theory, it is believed that these difficult to form chemical bonds cause the inactivation of at least a portion of the hydrogenation metal atoms, which results in a decrease in the number of large hydrogenation metal atomic clusters present on the catalyst. These clusters of hydrogenation metal atoms are called "ensembles" and when the hydrogen atoms chemically bond to the hydrogenation metal, the "ensembles" are effectively divided into "ensembles" of smaller size. Some chemical reactions, such as hydrogenolysis, require a certain minimum "ensemble" size to proceed. These reactions are sometimes referred to as "structure sensitive reactions." Therefore, when enough of the hydrogen bonds are formed, "ensemble" sizes are reduced enough to limit the hydrogenolysis activity of the catalyst. Regardless of the theory proposed, the catalysts prepared by the process have one or more of the improved properties that are disclosed herein.

Conversion

The catalysts prepared by the process of the present invention can be used as a catalyst for a variety of organic, e.g., hydrocarbon compound, conversion processes including cracking, those involving dewaxing of hydrocarbon feedstocks; isomerization of alkylaromatics, e.g., xylene isomerization; oligomerization of olefins to form gasoline, distillate, lube oils or chemicals; alkylation of aromatics; transalkylation of aromatics, e.g. toluene disproportionation; conversion of oxygenates to hydrocarbons; rearrangement of oxygenates; and conversion of light paraffins and olefins to aromatics, e.g., naphtha reforming. Non-limiting examples include: cracking hydrocarbons with reaction conditions including a temperature of from about 300° C. to about 700° C., a pressure of from about 0.1 atmosphere (bar) to about 30 atmospheres and weight hourly space velocity of from about 0.1 hr$^{-1}$ to about 20 hr$^{-1}$; dehydrogenating hydrocarbon compounds with reaction conditions including a temperature of from about 300° C. to about 700° C., a pressure of from about 0.1 atmosphere (bar) to about 10 atmospheres and weight hourly space velocity of from about 0.1 hr$^{-1}$ to about 20 hr$^{-1}$; converting paraffins to aromatics with reaction conditions including from about 300° C. to about 700° C., a pressure of from about 0.1 atmosphere (bar) to about 60 atmospheres and weight hourly space velocity of from about 0.5 hr$^{-1}$ to about 400 hr$^{-1}$ and a hydrogen/hydrocarbon mole ratio of from about 0 to about 20; converting olefins to aromatics, e.g., benzene, toluene and xylene, with reaction conditions including a temperature from about 100° C. to about 700° C., a pressure of from about 0.1 atmosphere (bar) to about 60 atmospheres, weight hourly space velocity of from about 0.5 hr$^{-1}$ to about 400 hr$^{-1}$, and a hydrogen/hydrocarbon mole ratio of from about 0 to about 20; converting alcohols, e.g., methanol, or ethers, e.g., dimethylether, or mixtures thereof to hydrocarbons, including olefins and/or aromatics with reaction conditions including a temperature from about 275° C. to about 600° C., a pressure of from about 0.5 atmosphere (bar) to about 50 atmospheres, weight hourly space velocity of from about 0.5 hr$^{-1}$ to about 100 hr$^{-1}$; isomerizing xylene feedstock components with reaction conditions including a temperature from about 230° C. to about 510° C., a pressure of from about 3 atmosphere (bar) to about 35 atmospheres, weight hourly space velocity of from about 0.1 hr$^{-1}$ to about 200 hr$^{-1}$, and a hydrogen/hydrocarbon mole ratio of from about 0 to about 100; disproportionating toluene with reaction conditions including a temperature from about 200° C. to about 760° C., a pressure of from about atmospheric to about 60 atmospheres, weight hourly space velocity of from about 0.08 hr$^{-1}$ to about 20 hr$^{-1}$; alkylating aromatic hydrocarbons, e.g., benzene and alkylbenzenes in the presence of an alkylating agent, e.g., olefins, formaldehyde, alkyl halides and alcohols, with reaction conditions including a temperature from about 250° C. to about 500° C., a pressure of from about atmospheric to about 200 atmospheres, weight hourly space velocity of from about 2 hr$^{-1}$ to about 2000 hr$^{-1}$, and an aromatic hydrocarbon/alkylating agent mole ratio of from about 1/1 to about 20/1; and transalkylating aromatic hydrocarbons in the presence of polyalkylaromatic hydrocarbons with reaction conditions including a temperature from about 340° C. to about 500° C., a pressure of from about atmospheric to about 200 atmospheres, weight hourly space velocity of from about 10 hr$^{-1}$ to about 1000 hr$^{-1}$, and an aromatic hydrocarbon/polyalkylaromatic hydrocarbon mole ratio of from about 1/1 to about 16/1.

In general, therefore, catalytic conversion conditions over a catalyst comprising the modified zeolite prepared by the present method include a temperature from about 100° C. to about 760° C., a pressure of from about 0.1 atmosphere (bar) to about 200 atmospheres (bar), weight hourly space velocity of from about 0.08 $hr^{-1}$ to about 2000 $hr^{-1}$, and a hydrogen/organic, e.g., hydrocarbon compound, molar ratio of from about 0 to about 100.

The catalyst finds particular application in the dealkylation of ethylbenzene to form benzene and ethane. In this process, an ethylbenzene-containing feed is contacted with the catalyst under ethylbenzene dealkylation conditions. Exemplary conditions include a temperature from 204° C. to 538° C. (400° F. to 1000° F.), a pressure of from 0.034 to 6.9 MPag (50 to 1000 psig) and a weight hourly space velocity (WHSV) of 0.1 to 100.

The catalyst finds particular application for isomerizing one or more xylene isomers in a $C_8$ aromatic feed containing ethylbenzene to obtain ortho-, meta-, and para-xylene in a ratio approaching the equilibrium value while substantially converting ethylbenzene to benzene and ethane. In particular, xylene isomerization is used in conjunction with a separation process to manufacture para-xylene. For example, a portion of the para-xylene in a mixed $C_8$ aromatics stream may be recovered using processes known in the art, e.g., crystallization, adsorption, etc. The resulting stream is then reacted under xylene isomerization conditions to restore ortho-, meta-, and paraxylenes to a near equilibrium ratio. At the same time, it is also desirable that ethylbenzene in the feed be removed by converting the ethylbenzene to benzene and ethane. The isomerization process is carried out by contacting a $C_8$ aromatic stream containing one or more xylene isomers and ethylbenzene, with the catalyst under isomerization conditions. The catalyst of the present invention is useful in saturating ethylene formed during ethylbenzene dealkylation and offers the benefit of reduced aromatics saturation and reduced cracking of light hydrocarbon gases.

In the vapor phase, suitable isomerization conditions include a temperature in the range 250° C. to 600° C., preferably 300° C. to 550° C., a pressure of from 0.034 to 6.9 MPag (50 to 1000 psig) and a weight hourly space velocity (WHSV) of 0.1 to 100, preferably 0.5 to 50. Optionally, isomerization in the vapor phase is conducted in the presence of 0.1 to 30.0 moles of hydrogen per mole of alkylbenzene.

The xylene isomerization reaction can be carried out in a fixed bed reactor containing the catalyst. The xylene isomerization reaction can also be carried out in sequential beds using two catalysts. Such processes are disclosed in U.S. Pat. Nos. 4,899,011 and 5,516,956, which are hereby incorporated by reference. In this embodiment, each catalyst is in a separate bed or one of the catalysts forms one part of a bed, while the second catalyst forms the remaining part of the bed and is located downstream with respect to the first catalyst. The first catalyst is used primarily for ethylbenzene conversion while the second catalyst is used primarily for xylene isomerization. In this embodiment, the catalyst prepared by the process of the present invention is preferably the first catalyst and the second catalyst is one that is specifically adapted for xylenes isomerization. In this embodiment, the first catalyst will preferably comprise from about 10 percent to about 90 percent of the bed volume.

The catalyst finds particular application in the transalkylation of polyalkylaromatic hydrocarbons. In particular, a catalyst comprising a molecular sieve having an intermediate pore size, e.g., ZSM-12, and a hydrogenation metal, e.g., platinum, palladium or rhenium, is useful in the catalytic conversion of $C_9$+alkylaromatic hydrocarbons, either alone or in the presence of toluene and/or benzene, to produce xylenes. Such conversion is typically effected at a temperature of from about 340 to 510° C. (650 to about 950° F.), and preferably from about 400 to 450° C. (750 to about 850° F.), a pressure of from about 790 to 4240 kPa (100 to about 600 psig), and preferably from about 1480 to 3550 kPa (200 to about 500 psig), a weight hourly space velocity (WHSV) of between about 0.1 and about 200 $hr^{-1}$, and preferably between about 0.5 and about 20 $hr^{-1}$, and a hydrogen, $H_2$, to hydrocarbon, HC, molar ratio of between about 1 and about 5, and preferably from about 1 to about 3.

Where a catalyst comprising ZSM-12 and a hydrogenation metal is used in the catalytic conversion of $C_9$+ alkylaromatic hydrocarbons, the catalyst may be used in combination with a second catalyst comprising a molecular sieve having an intermediate pore size, e.g., ZSM-5, ZSM-11, ZSM-22, ZSM-23, ZSM-35, ZSM-48, ZSM-57 and ZSM-58. The first catalyst and second catalyst may be arranged in separate catalyst beds, with the feed cascading from the catalyst bed containing the first catalyst comprising ZSM-12 and the hydrogenation metal to the bed containing the second molecular sieve, e.g., ZSM-5. Alternatively, the first catalyst and second catalyst can be combined in a single catalyst bed.

The process of the present invention finds particular application in the vapor phase disproportionation of toluene. Such vapor phase disproportionation comprises contacting a feed stream containing toluene under disproportionation conditions with a hydrogen treated catalyst comprising the crystalline molecular sieve and at least one hydrogenation metal selected from the group consisting of a Group VIIB metal, a Group VIII metal, to yield a product mixture which comprises a mixture of unreacted (unconverted) toluene and benzene and xylene.

In a preferred embodiment, the catalyst is selectivated to produce enhanced amounts of para-xylene. When coke is the selectivating agent, selectivation may be accomplished by exposing the catalyst in a reactor bed to a thermally decomposable organic compound, e.g., toluene, at a temperature in excess of the decomposition temperature of said compound, e.g., from about 480° C. to about 650° C., more preferably 540° C. to 650° C., at a WHSV in the range of from about 0.1 to 20 lbs of feed per pound of catalyst per hour, at a pressure in the range of from about 1 to 100 atmospheres, and in the presence of 0 to about 2 moles of hydrogen, more preferably from about 0.1 to about 2 moles of hydrogen per mole of organic compound, and optionally in the presence of 0-10 moles of nitrogen or another inert gas per mole of organic compound. This process is conducted for a period of time until a sufficient quantity of coke has deposited on the catalyst surface, generally at least about 2% by weight and more preferably from about 8 to about 40% by weight of coke.

The disproportionation is usually carried out at conditions which include a temperature between about 375° C. and 550° C., more preferably between about 400° C. and 485° C., at a hydrogen to toluene mole ratio of from 0 to about 10, preferably between about 0.1 and 5 and more preferably from about 0.1 to about 1, at a pressure between about 1 atmosphere and about 100 atmospheres and utilizing a WHSV of between about 0.5 and about 50.

The disproportionation process may be conducted as a batch, semi-continuous or continuous operation using a fixed or moving bed catalyst system deposited in a reactor bed. The catalyst may be regenerated after coke deactivation by burning off the coke to a desired extent in an oxygen-containing atmosphere at elevated temperatures as known in the art.

The following examples illustrate the invention:

EXAMPLE 1

A test was carried out using a silica bound ZSM-5 catalyst containing 0.5 weight percent of rhenium. The hydrogen treatment was carried out by contacting the catalyst with hydrogen at a temperature of 482° C. The treatment was carried out for a period of 4 hours and at a pressure of 1723 kPa. Next, the hydrogen-treated catalyst was contacted with simulated reformer feed. The reformer feed contained $C_2$-$C_5$ hydrocarbons ($C_2$=21.31% wt., Ethane=35.2% wt, Propane=25.09%, $C_4$=12.36%, $C_5$=4.74%, and olefins=1.3%). Light gas make and reactor deltaT was tracked during the heat up period. The light-off temperature is the temperature at which considerable methane starts appearing, which indicates significant hydrogenolysis activity. The results of the test are shown as Test A in Table 1 below.

For comparison, the test was carried out in the same manner as Test A, except the catalyst did not undergo the hydrogen treatment. The results of the test are shown as Test B in Table 1 below.

TABLE 1

| Test | Light-off Temperature | Maximum $C_2$/$C_3$ Conversion (Temperature, ° C.) |
|---|---|---|
| A | 260° C. | 85% / 75% (310° C.) |
| B | 232° C. | 100% / 100% (282° C.) |

The results in Table 1 show that both the light-off and maximum $C_2$/$C_3$ conversion temperature were higher for the hydrogen treated catalyst, which indicates that the hydrogen treated catalyst had less hydrogenolysis activity. Also indicative of the lower hydrogenolysis activity of Test A is that the maximum $C_2$/$C_3$ conversion is less than the 100% set forth in Test B.

EXAMPLE 2

Two different catalysts were treated with hydrogen at different conditions of time and temperature. The conditions used in the tests are shown below in Table 2. The catalyst used in Test A comprised a ZSM-5 catalyst containing 0.5 weight percent of rhenium. The catalyst used in Test B comprised a silica bound ZSM-5 catalyst containing 0.5 weight percent of rhenium. After hydrogen treatment, the treated catalysts were tested for ethane hydrogenolysis by contacting the catalysts with a feed comprising 80 mol % hydrogen and 20 mole % ethane. The results of the tests are shown below in Table 2.

TABLE 2

| Test | Hydrogen Treatment Conditions Before Exposure to Ethane | Ethane Conversion (Temperature° C.) |
|---|---|---|
| Test A (Pressure = 1551 kPa) | Heat up in $H_2$ to 260° C. in 7 hrs. | |
| | Heatup to 349° C. and hold under $H_2$ for 14 hrs. | 99% (349° C.) |
| | Ramp up to 413° C. F in 45 minutes | 99% (413° C.) |
| Test B (Pressure = 1723 kPa) | Heatup in $H_2$ to 316° C. in 7 hrs | |
| | Hold at 316° C. for 21 hrs then ramp to 349° C. in 2 hrs | 75% (349° C.) |
| | Hold at 349° C. for 15 hrs | <1% (349° C.) |
| | Ramp to 413° C. in 3 hrs | <1% (413° C.) |

The results in Table 2 show that higher temperature, higher pressure, and longer hydrogen treatments can substantially eliminate ethane hydrogenolysis activity.

EXAMPLE 3

Catalysts were hydrogen treated and tested in the dealkylation of ethylbenzene. The catalyst used in Test A, Test B and Test C comprised ZSM-5 and 0.5 weight percent of rhenium. The hydrogen treatment conditions are shown below in Table 3. The hydrogen treatment in Test A was least severe. The hydrogen treatment in Test B was more severe. The hydrogen treatment in Test C was most severe. The conditions used in the ethylbenzene dealkylation were a $H_2$ to feed ratio of 1, a $H_2$ partial pressure of 120 psia, and a WHSV of 10. Ethylbenzene conversion was from 75 to 85 percent. The results of the tests are shown below in Table 3.

TABLE 3

| Test | $H_2$ Treatment | De-edging Time (Time of Oil on System) | Days on Stream | $H_2$ pressure | Product Benzene Purity | Aromatic Ring Loss | Methane (% of $C_1$-$C_5$) Formed |
|---|---|---|---|---|---|---|---|
| A | Heat up in $H_2$ from 121° C. to 399° C. over 6 hrs (P = 1462 kPa) | 2 days (779 kPa-a $H_2$) | 10 | 1041 kPa-a | 99.88% | 0.63% | 3.6 |
| B | Heat up in $H_2$ from 121° C. to 393° C. over 6 hrs (P = 1551 kPa), soak at 393° C. for 5 hrs (P = 1551-3033 kPa) | 5 days | 6 | 1172 kPa-a | 99.93% | 0.43% | <0.3 |

TABLE 3-continued

| Test | H$_2$ Treatment | De-edging Time (Time of Oil on System) | Days on Stream | H$_2$ pressure | Product Benzene Purity | Aromatic Ring Loss | Methane (% of C$_1$-C$_5$) Formed |
|---|---|---|---|---|---|---|---|
| C | Heat up in H$_2$ from 121° C. to 393° C. over 6 hrs (P = 1551 kPa), soak at 393° C. for 5 hrs (P = 1551-3033 kPa), soak at 427° C. for 16 hrs (P = 1551 kPa) | 1 day | 1.5 | 1172 kPa-a | 99.93% | 0.40% | <0.3 |

In ethylbenzene dealkylation, it is important to produce high purity benzene with low ring loss, and low hydrogenolysis of C$_2$ to C$_5$ hydrocarbons. The results in Table 3 show that the hydrogen pretreatments reduced the amount of de-edging time, improved the product benzene purity, reduced aromatic ring loss and reduced the hydrogenolysis of C$_2$-C$_5$ gases to methane.

What is claimed is:

1. A process for reducing the addition hydrogenation activity of a catalyst comprising a crystalline molecular sieve and at least one hydrogenation metal selected from the group consisting of a Group VIIB metal, a Group VIII metal, and mixtures thereof, said process comprising:
   treating the catalyst with a catalyst treatment feed consisting of hydrogen before the catalyst is put on stream for an organic conversion under sufficient conditions of temperature and pressure and for a time of at least 4 hours to reduce the addition hydrogenation activity of the treated catalyst in an amount of at least 10 percent in comparison to the untreated catalyst.

2. The process recited in claim 1, wherein said molecular sieve has an intermediate pore size.

3. The process recited in claim 2, wherein said molecular sieve has a structure selected from the group consisting of MFI, MEL, MTW, EUO, MTT, HEU, FER, MFS, and TON.

4. The process recited in claim 1, wherein said molecular sieve is selected from the group consisting of ZSM-5, ZSM-12, ZSM-22, ZSM-23, ZSM-34, ZSM-35, ZSM-38, ZSM-48, ZSM-50, and ZSM-57.

5. The process recited in claim 4, wherein the addition hydrogenation activity of the treated catalyst is reduced at least 40 percent in comparison to the untreated catalyst.

6. The process recited in claim 4, wherein the addition hydrogenation activity of the treated catalyst is reduced at least 50 percent in comparison to the untreated catalyst.

7. The process recited in claim 2, wherein the conditions include a pressure of at least 700 kPa, a temperature of at least 316° C., and a time of at least 4 hours.

8. The process recited in claim 2, wherein the conditions include a pressure of at least 1034 kPa, a temperature of at least 371° C., and a time of at least 8 hours.

9. The process recited in claim 2, wherein the conditions include a pressure of at least 1400 kPa, a temperature of at least 427° C., and a time of at least 10 hours.

10. The process recited in claim 7, wherein said hydrogenation metal is present in said catalyst in an amount of from about 0.03 to about 3 percent by weight based on the total weight of said catalyst.

11. The process recited in claim 10, wherein said hydrogenation metal is selected from the group consisting of platinum, rhenium, and mixtures thereof.

12. The process recited in claim 11, wherein said hydrogenation metal is incorporated with said molecular sieve by ion exchange.

13. The process recited in claim 7, wherein said crystalline molecular sieve is MFI.

14. The process recited in claim 13, wherein said catalyst further comprises a binder.

15. The process recited in claim 14, wherein said binder is silica or alumina.

16. The process recited in claim 13, wherein the addition hydrogenation activity of the treated catalyst is reduced at least 75 percent in comparison to the untreated catalyst.

17. The process recited in claim 16, wherein said crystalline molecular sieve is ZSM-5.

18. The process recited in claim 13, wherein said catalyst further comprises a selectivating agent to enhance the para-selectivity of said catalyst.

19. The process recited in claim 18, wherein said selectivating agent is selected from the group consisting of phosphorus, an alkaline earth metal oxide, boron oxide, titania, antimony oxide, silica, manganese oxide, and coke.

20. The process recited in claim 17, wherein said hydrogenation metal is rhenium.

21. The process recited in claim 17, wherein the treated catalyst is substantially free of addition hydrogenation activity.

22. The process recited in claim 11, wherein said crystalline molecular sieve is ZSM-12.

23. A process for treating a catalyst comprising ZSM-5 and least one hydrogenation metal selected from the group consisting of platinum, rhenium, and mixtures thereof to reduce the addition hydrogenation activity of the catalyst, said process comprising:
   treating the catalyst with a catalyst treatment feed consisting essentially of hydrogen before the catalyst is put on stream for an organic conversion at a pressure of at least 700 kPa, a temperature of at least 316° C., and a time of at least 4 hours to reduce the addition hydrogenation activity of the treated catalyst in an amount at least 25 percent in comparison to the untreated catalyst.

24. The process recited in claim 23, wherein the addition hydrogenation activity of the treated catalyst is reduced at least 75 percent in comparison to the untreated catalyst.

25. The process recited in claim 23, wherein said hydrogenation metal is rhenium.

26. The process recited in claim 24, wherein said catalyst further comprises binder selected from the group consisting of silica and alumina.

27. A process for reducing the addition hydrogenation activity of a catalyst comprising ZSM-12 and at least one hydrogenation metal selected from the group consisting of platinum, rhenium, and mixtures thereof, said process comprising:

treating the catalyst with a catalyst treatment feed consisting of hydrogen before the catalyst is put on stream for an organic conversion at a pressure of at least 700 kPa, a temperature of at least 316° C., and a time of at least 4 hours to reduce the addition hydrogenation activity of the treated catalyst in an amount at least 25 percent in comparison to the untreated catalyst.

* * * * *